US012582133B2

(12) United States Patent
Janzen et al.

(10) Patent No.: US 12,582,133 B2
(45) Date of Patent: Mar. 24, 2026

(54) USE OF ST GAL(+) BACTERIA FOR PRODUCING A FERMENTED MILK PRODUCT WITH A RELATIVELY HIGH STABLE pH

(71) Applicant: Chr. Hansen A/S, Hoersholm (DK)

(72) Inventors: Thomas Janzen, Hoersholm (DK); Ditte Ellegaard Christiansen, Hoersholm (DK)

(73) Assignee: Chr. Hansen A/S, Hoersholm (DK)

( * ) Notice: Subject to any disclaimer, the term of this patent is extended or adjusted under 35 U.S.C. 154(b) by 803 days.

(21) Appl. No.: 17/620,649

(22) PCT Filed: Jun. 19, 2020

(86) PCT No.: PCT/EP2020/067150
§ 371 (c)(1),
(2) Date: Dec. 17, 2021

(87) PCT Pub. No.: WO2020/254604
PCT Pub. Date: Dec. 24, 2020

(65) Prior Publication Data
US 2022/0312785 A1 Oct. 6, 2022

(30) Foreign Application Priority Data
Jun. 20, 2019 (EP) .................................... 19181466

(51) Int. Cl.
*A23C 9/123* (2006.01)
*C12N 1/20* (2006.01)
(Continued)

(52) U.S. Cl.
CPC ............ *A23C 9/1238* (2013.01); *C12N 1/205* (2021.05); *C12N 9/1205* (2013.01); *C12N 15/01* (2013.01);
(Continued)

(58) Field of Classification Search
CPC .......... C12N 1/20; C12N 1/205; C12N 15/01; C12N 9/1205; A23C 19/0323; A23C 9/1238; C12R 2001/46; A23V 2400/249
(Continued)

(56) References Cited

U.S. PATENT DOCUMENTS

| | | | |
|---|---|---|---|
| 8,865,238 B2 | 10/2014 | Janzen et al. | |
| 9,060,524 B2 | 6/2015 | Janzen et al. | |

(Continued)

FOREIGN PATENT DOCUMENTS

| | | |
|---|---|---|
| EP | 2 957 180 B1 | 12/2015 |
| WO | WO-2011/026863 A1 | 3/2011 |

(Continued)

OTHER PUBLICATIONS

Anbukkarasi, K. et al.; "Production of low browning Mozzarella cheese: Screening and characterization of wild galactose fermenting Streptococcus thermophilus strains"; International Journal of Advanced Research, vol. 1, Issue 5; Jul. 2013; pp. 83-96.
(Continued)

*Primary Examiner* — Subbalakshmi Prakash
(74) *Attorney, Agent, or Firm* — Yoshimi D. Barron

(57) ABSTRACT
A method for producing a fermented milk product (e.g. a yogurt) with a relatively high stable pH value at the end of the fermentation comprising inoculating milk with *Streptococcus thermophilus* (ST) Gal(+) bacteria.

12 Claims, 3 Drawing Sheets

Figure 1:
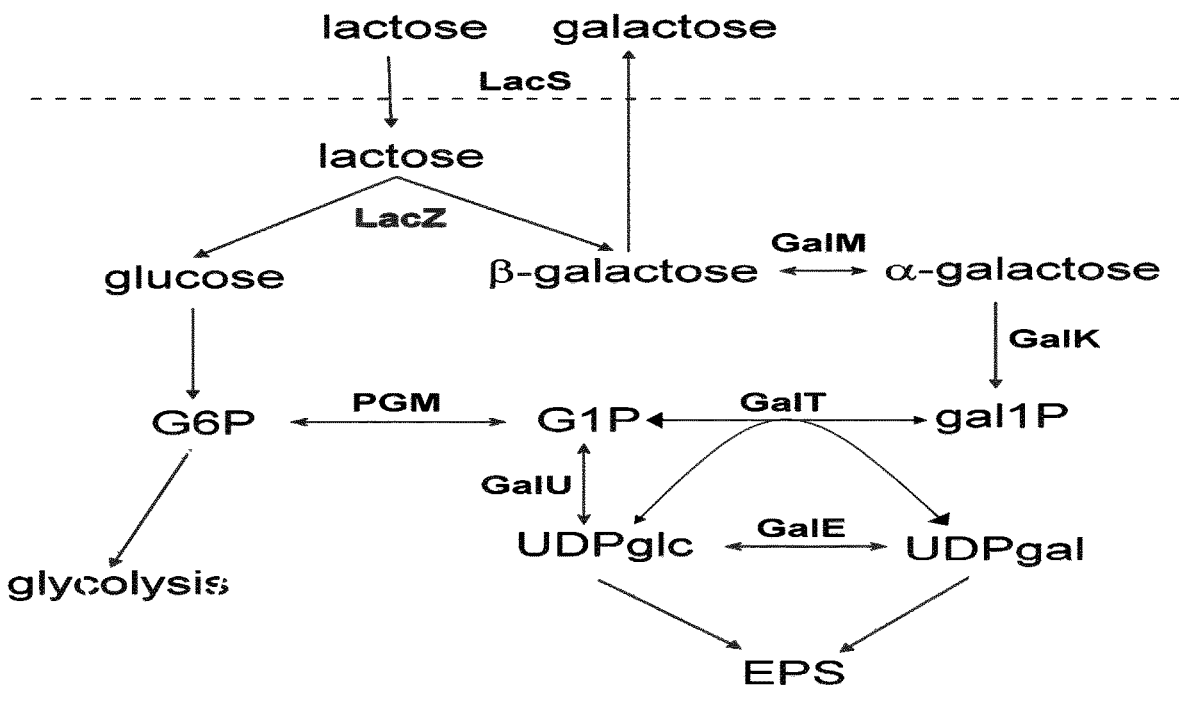

Specification includes a Sequence Listing.

(51) Int. Cl.

| | |
|---|---|
| *C12N 1/205* | (2026.01) |
| *C12N 9/12* | (2006.01) |
| *C12N 15/01* | (2006.01) |
| *C12R 1/46* | (2006.01) |

(52) U.S. Cl.
CPC ..... *A23V 2400/249* (2023.08); *C12R 2001/46* (2021.05)

(58) Field of Classification Search
USPC .......................................................... 426/43
See application file for complete search history.

(56) References Cited

U.S. PATENT DOCUMENTS

| | | | |
|---|---|---|---|
| 9,416,351 | B2 | 8/2016 | Janzen et al. |
| 9,562,221 | B2 | 2/2017 | Janzen et al. |
| 2012/0164275 | A1 | 6/2012 | Janzen et al. |
| 2017/0096635 | A1 | 4/2017 | Janzen et al. |
| 2017/0135360 | A1 | 5/2017 | Garrigues et al. |
| 2017/0298457 | A1 | 10/2017 | Janzen et al. |
| 2019/0343138 | A1 | 11/2019 | Ba et al. |
| 2020/0375207 | A1 | 12/2020 | Janzen et al. |
| 2021/0274800 | A1 | 9/2021 | Bloch et al. |

FOREIGN PATENT DOCUMENTS

| | | |
|---|---|---|
| WO | WO-2011/092300 A1 | 8/2011 |
| WO | WO-2018/130630 A1 | 7/2018 |
| WO | WO-2018/177835 A1 | 10/2018 |
| WO | WO-2019/042881 A1 | 3/2019 |

OTHER PUBLICATIONS

Anbukkarasi, Kaliyaperumal et al.; "Preparation of low galactose yogurt using cultures of Gal *Streptococcus thermophilus* in combination with Lactobacillus delbrueckii ssp. *bulgaricus*"; J Food Sci Technol (Sep. 2014) 51(9):2183-2189.

Chr. Hansen A/S; "Cheese Culture Catalogue DVS Product Range"; Jan. 1, 2014; 68 pages.

Derkx, Patrick M.F. et al.; "The art of strain improvement of industrial lactic acid bacteria without the use of recombinant DNA technology"; Microbial Cell Factories 13(Suppl 1); Aug. 29, 2014; 13 pages.

Yoflex Acidifix of Chr. Hansen A/S www.chr-hansen.com/en/food-cultures-and-enzymes/fresh-dairy/cards/product; accessed Nov. 10, 2018; 1 page.

```
                       SEQUENCE LISTING

<160> NUMBER OF SEQ ID NOS: 8

<210> SEQ ID NO 1
<211> LENGTH: 6
<212> TYPE: DNA
<213> ORGANISM: Streptococcus thermophilus

<400> SEQUENCE: 1 tacgat                                                              6

<210> SEQ ID NO 2
<211> LENGTH: 6
<212> TYPE: DNA
<213> ORGANISM: Streptococcus thermophilus

<400> SEQUENCE: 2 tatgat                                                              6

<210> SEQ ID NO 3
<211> LENGTH: 6
<212> TYPE: DNA
<213> ORGANISM: Streptococcus thermophilus

<400> SEQUENCE: 3 tattat                                                              6

<210> SEQ ID NO 4
<211> LENGTH: 6
<212> TYPE: DNA
<213> ORGANISM: Streptococcus thermophilus

<400> SEQUENCE: 4 tactat                                                              6

<210> SEQ ID NO 5
<211> LENGTH: 70
<212> TYPE: DNA
<213> ORGANISM: Streptococcus thermophilus

<400> SEQUENCE: 5
aaaatattga ttttccatgt gaaaggggtt atgatttcag tataaacaaa aagaataagt     60
gagatacatc                                                          70

<210> SEQ ID NO 6
<211> LENGTH: 70
```

-continued

```
<212> TYPE: DNA
<213> ORGANISM: Streptococcus thermophilus

<400> SEQUENCE: 6
aaaatattga ttttccatgt gaaaggggtt acgatttcag tataaacaaa aagaataagt          60
gagatacatc                                                                70

<210> SEQ ID NO 7
<211> LENGTH: 70
<212> TYPE: DNA
<213> ORGANISM: Streptococcus thermophilus

<400> SEQUENCE: 7
aaaatattga ttttccatgt gaaaggggtt acgatttcag tataaacaaa aagaataagt          60
gagatacatc                                                                70

<210> SEQ ID NO 8
<211> LENGTH: 70
<212> TYPE: DNA
<213> ORGANISM: Streptococcus thermophilus

<400> SEQUENCE: 8
aaaatattga ttttccatgt gaaaggggtt acgatttcag tataaacaaa aagaataagt          60
gagatacatc                                                                70
```

USE OF ST GAL(+) BACTERIA FOR PRODUCING A FERMENTED MILK PRODUCT WITH A RELATIVELY HIGH STABLE pH

CROSS-REFERENCE TO RELATED APPLICATIONS

The present application is the U.S. National Stage of International Application No. PCT/EP2020/067150, filed Jun. 19, 2020, and claims priority to European Patent Application No. 19181466.4, filed Jun. 20, 2019.

FIELD OF THE INVENTION

The present invention relates to a method for producing a fermented milk product (e.g. a cheese or a yogurt) with a relatively high stable pH value at the end of the fermentation comprising inoculating milk with *Streptococcus thermophilus* (ST) Gal(+) bacteria.

BACKGROUND ART

The food industry uses numerous bacteria, in particular lactic bacteria, to improve e.g. the taste and the texture of foods. In the case of the dairy industry, lactic acid bacteria (LAB) are used intensively to bring about the acidification of milk (by fermentation) but also to e.g. texturize the product into which they are incorporated.

Control of post-acidification is of significant commercial relevant importance.

In the art the term "post-acidification" generally is described as relating to the production of lactic acid by the LAB after the termination of fermentation—for instance paragraph [0005] of EP2957180B1 (Chr. Hansen A/S, Denmark) reads:

"Even in methods comprising a rapid cooling step, post-acidification is observed, i.e. the production of lactic acid by the LAB after the termination of fermentation, i.e. after the desired pH has been reached. Post-acidification is considered to represent one of the most important problems during fermentation of milk products today. The further decrease of pH value during processing and storage of the fermented milk product leads to problems with elevated acidity and reduced shelf life."

Many current methods for producing fermented milk products can be characterized by the following series of steps:

(a) milk is fermented using a starter culture comprising lactic acid bacteria (or LAB) capable of metabolizing glucose obtained from lactose present in the milk;

(b) the fermentation causes the production of lactic acid, which causes a decrease of the pH from initially 6.4 to 6.8 (for cow milk) to a range between pH 3.8 and 4.2;

(c) the fermentation is terminated by rapid cooling of the fermented milk product once the pH desired for the fermented product at issue has been reached.

This method is for example used to produce cheese, yoghurt and yoghurt beverages.

The rapid cooling of the fermented milk product at a predetermined pH value is carried out to terminate fermentation. Without cooling of the fermented product, the fermentation would continue. However, rapid cooling may have disadvantages, as it e.g. may lead to loss of texture.

To e.g. avoid the rapid cooling step—the prior art describes numerous different technical solutions for improved control of post-acidification.

An example of a herein relevant commercially available product is the YOFLEX® ACIDIFIX® culture of Chr. Hansen A/S, Denmark, which is a product that "Improve quality and shelf life with the superior pH stability" (see e.g. www.chr-hansen.com). As understood by the skilled person in the present context—improved shelf life due to superior pH stability relates to improved control of post-acidification.

EP2957180B1 (Chr. Hansen A/S, Denmark) describes different technical solutions for improved control of post-acidification, such as e.g.:

use of *L. bulgaricus* strains with a deficiency in amino acid metabolism and/or the use of specific LAB strains characterized by weakly post-acidifying activity—see e.g. [0007];

control of the buffering capacity and the maintenance of the buffering capacity and the pH within a predetermined range during fermentation—see e.g. [0008];

use of lactose deficient (Lac(−)) *Streptococcus thermophilus* (ST) and *Lactobacillus delbrueckii* ssp. bulgaricus strains—see e.g. claim 1.

As known in the art, in the species *S. thermophilus* (ST) galactose is excreted via the lactose/galactose system (see schematic drawing of lac/gal metabolism in FIG. 1 herein). For 1 mol of lactose taken up by the cell 1 mol of galactose may be excreted.

As known in the art, *Streptococcus thermophilus* (ST) strains are normally not able to significantly reduce the amounts of excreted galactose in milk—i.e. they are what in the art and herein may be termed "ST Gal(−) bacteria"—see e.g. the article of Anbukkarasi et al. (J Food Sci Technol (September 2014) 51(9):2183-2189), which reads in the abstract:

"Most strains of *S. thermophilus* are galactose negative (Gal−) and are able to metabolize only glucose portion of lactose and expel galactose into the medium. This metabolic defect leads to the accumulation of free galactose in yogurt, resulting in galactosemia among consumers. Hence there is an absolute need to develop low galactose yogurt. Therefore, in this study, three galactose positive (Gal+) *S. thermophilus* strains . . . were used for preparation of low galactose yogurt."

All the ST strains as described in above discussed EP2957180B1 (Chr. Hansen A/S) and above discussed product YOFLEX® ACIDIFIX® are what the skilled person and herein is considered to be ST Gal(−) bacteria.

A relatively high concentration of galactose can result in "browning" during heating of cheeses as it is often described when e.g. mozzarella cheese is produced *by S. thermophilus* (ST) for e.g. pizza production.

The prior art describes that some *S. thermophilus* (ST) so-called galactose positive strains (herein termed "ST Gal (+) bacteria") may be used for reducing possible browning problems for a cheese (e.g. mozzarella) used in a process (e.g. for making pizza) involving a significant heating step (e.g. to a temperature above 70° C.)—see e.g. the article of Anbukkarasi et al. ("Production of low browning Mozzarella cheese: Screening and characterization of wild galactose fermenting *Streptococcus thermophilus* strains", International Journal of advanced research, 2013, vol. 1, no. 5, pp. 83-96).

As known to the skilled person in the present context—"reducing possible browning" and "improved control of post-acidification" are significantly different problems that may e.g. be relevant to different dairy products.

For instance, browning problems may normally preferably be relevant for a cheese (e.g. mozzarella) used in a process (e.g. for making pizza) involving a significant heating step (e.g. to a temperature above 70° C.).

To the contrary, post-acidification issues are relevant for dairy products that are produced without involving use of a significant heating step (e.g. to a temperature above 70° C.)—such as e.g. cheese, yogurt.

The article of Derkx et al. ("The art of strain improvement of industrial lactic acid bacteria without the use of recombinant DNA technology"; Microbial Cell Factories 2014, 13 (Suppl 1)) is a review article that e.g. on page 9 discusses post-acidification issues and reads on page 9, left column:

"In another approach to obtain improved strains with reduced post-acidification the importance of the oligopeptide transport for growth fitness of *S. thermophilus* in milk was explored . . . and mutants exhibiting an altered oligopeptide transport system were found to have a reduced acidification rate".

The above referred article of Derkx et al. (2014) reads on page 9, top of right column: "In addition, excess free galactose can lead to post acidification problems and imbalance in the cheese flora due to growth of resident lactic acid bacteria. Galactose positive wild type strains or galactose fermenting mutants are therefore interesting, especially for the purpose of reducing browning in pizza cheese."

As understood by the skilled person in the present context, the post acidification problems discussed in above quoted paragraph of the Derkx et al. (2014) article relates to "growth of resident lactic acid bacteria"—i.e. production of lactic acid by the resident LAB after the termination of fermentation.

WO2011/026863A1 (Chr. Hansen) and WO2011/092300A1 (Chr. Hansen) describe that *S. thermophilus* (ST) strains with mutations in the galK (galactokinase) gene generate a higher viscosity in fermented milk. WO2019/042881A1 (Chr. Hansen) describes examples of some ST Gal(+) bacteria. None of these three WO publications describe/relate to herein discussed "post-acidification" related problems.

In summary, in the art are "post-acidification" problems generally described as relating to the production of lactic acid by the resident LAB after the termination of the fermentation as such and the art describes numerous different solutions relating to the controlling/reducing post-acidification issue—such as e.g. use of ST Lac(−) bacteria or use of ST bacteria with an altered oligopeptide transport system.

SUMMARY OF THE INVENTION

The problem to be solved by the present invention is to provide a method for producing a fermented milk product (e.g. a yogurt) with a relatively high stable pH value at the end of the fermentation and wherein an advantage of the produced fermented milk product (e.g. a yogurt) may e.g. be a lower post acidification during e.g. storage of the produced fermented milk product.

The solution is based on that the present inventors have identified a herein surprisingly relevant link between *S. thermophilus* (ST) galactose positive strains (herein termed "ST Gal(+) bacteria") and the possibility to obtain a stable relatively high pH at the end of the fermentation as such.

As discussed above, in the art are "post-acidification" problems generally described as relating to the production of lactic acid by the resident lactic acid bacteria (LAB) after the termination of the fermentation as such as e.g. under storage after the fermentation as such.

It is evident, that above discussed relatively high pH at the end of the fermentation as such of the surprising link discussed above is an effect initiated during the fermentation as such based on the growth profile of the Gal(+) ST bacteria.

Without being limited to theory—the present inventors are not aware of a single prior art document that directly and unambiguously describes the above mentioned surprising link between ST Gal(+) bacteria and the possibility to obtain a stable relatively high pH at the end of the fermentation as such.

Figure 2:
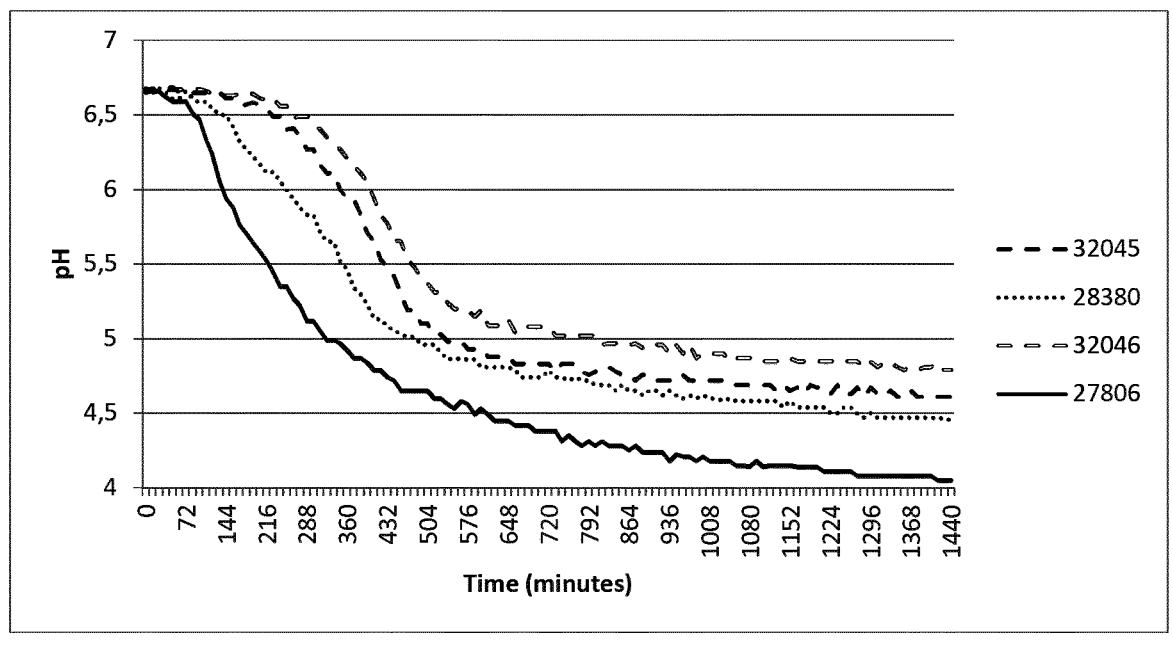
Figure 3:
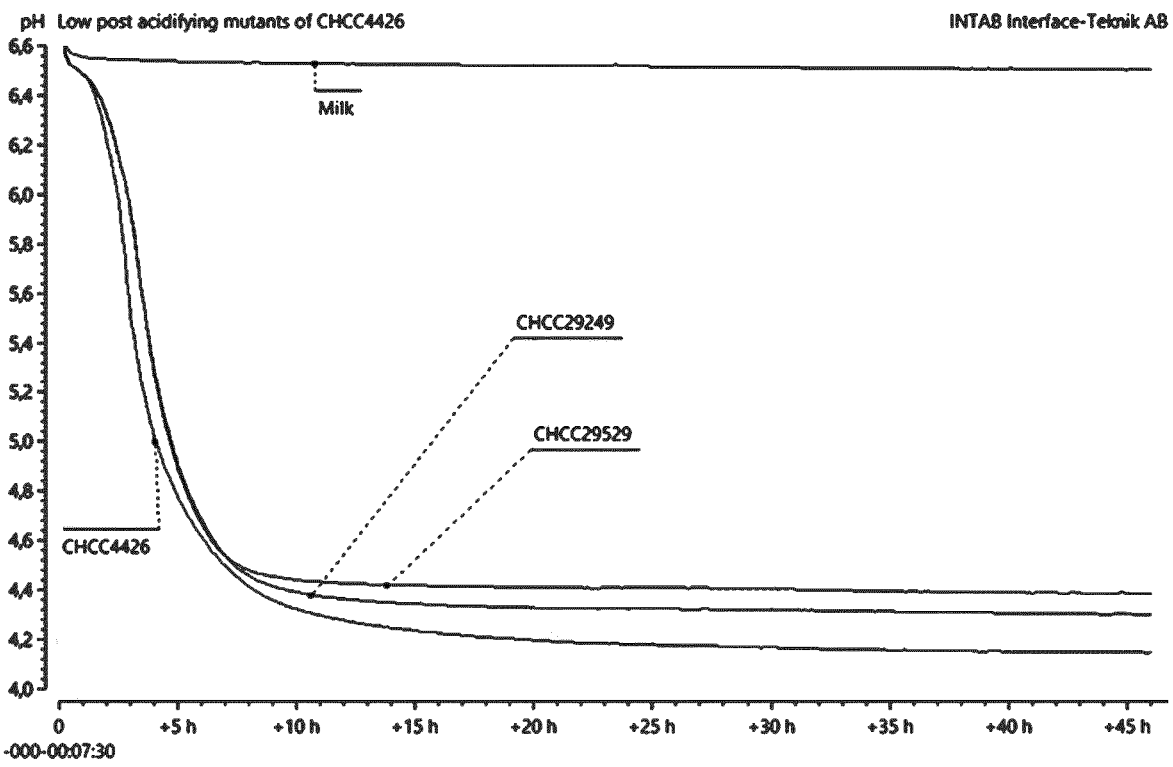

As discussed in e.g. working Examples herein and shown in e.g. FIGS. 2 and 3—herein described ST Gal(+) bacteria had a significantly higher stable pH (around 0.2 to 0.6 points) than corresponding wildtype ST Gal(−) bacteria at the end of the fermentation as such.

As can be seen in e.g. FIG. 2—use of ST Gal(+) bacteria as described herein gave a pH from 4.3 to 4.8 at the end of fermentation and use of wildtype CHCC27806 ST Gal(−) gave a pH around 4.15 (i.e. less than pH 4.3). Said in other words, use of the ST Gal(+) bacteria gave a significantly higher stable end pH (around 0.3 to 0.6 points) value than use of corresponding wildtype CHCC27806 ST Gal(−) strain.

Further, the initial acidification activity was relatively unchanged (see e.g. FIG. 2 or FIG. 3), which demonstrates that the observed low acidification activity (i.e. relatively high stable pH value at the end of the fermentation) is not due to a general lower acidification rate.

Without being limited to theory—it is believed that a higher final pH at the end of the fermentation as such would have an impact on post acidification during shelf life, which may be a significant problem with dairy products such as e.g. yogurt (see above).

Accordingly, herein discussed ST Gal(+) strains with a stable higher pH at the end of the fermentation would result in lower post acidification e.g. under storage which is a desired trait of e.g. commercial relevant dairy products.

One may say that the herein identified novel link between ST Gal(+) strains and the possibility to obtain a stable relatively high pH at the end of the fermentation as such may be said to "change behavior" of the skilled person—for instance, if one wants a "low post acidification" yogurt culture one would after the disclosure of the present invention choose a suitable ST Gal(+) bacteria instead of other prior art know different "low post acidification" cultures (see above).

As discussed in working Example herein—around 20% of the tested ST Gal(+) strains actually worked as required herein (i.e. gave herein discussed relatively high stable pH value at the end of the fermentation).

Accordingly, without the knowledge of the present invention the skilled person could easily have tested a ST Gal(+) strain of interest and not identified the herein relevant positive "stable relatively high pH at the end of the fermentation" effect.

However, once the herein discussed novel link between ST Gal(+) and the "stable relatively high pH at the end of the fermentation" effect has been disclosed by the present invention—it is routine screening/selection work for the skilled person to identify novel ST Gal(+) strains with this positive "stable relatively high pH at the end of the fermentation" effect.

One e.g. simply first isolate/select e.g. around 100 different ST Gal(+) strains by routine procedure and from this pool of different ST Gal(+) strains (with roughly 20% positive as disclosed herein) is then screened/selected for a ST Gal(+) strain having herein described positive "stable relatively high pH at the end of the fermentation" effect.

Accordingly and discussed in further details below—one may say that the present i invention is based on that the present inventors have developed a novel selection method for the identification of new ST Gal(+) strains having herein described positive "stable relatively high pH at the end of the fermentation" effect.

As discussed in working example below—the present inventors tried to identify a positive "stable relatively high pH at the end of the fermentation" ST strains based on a pool of different ST Gal(−) strains and did not identify a single positive strain/cell—i.e. without the knowledge of the present invention it would be impossible (or take very long time) to identify a ST strain having herein described positive "stable relatively high pH at the end of the fermentation" effect.

Accordingly, a first aspect of the invention relates to a method for producing a fermented milk product with a relatively high stable pH value at the end of the fermentation comprising following steps:

(a): inoculating at least 100 L milk with:

(I): a *Streptococcus thermophilus* (ST) bacteria composition comprising from $10^4$ to $10^{14}$ CFU/g ST bacteria cells, characterized by that the ST bacteria are able to reduce by at least 10% the amounts of excreted galactose in milk as compared to reference ST CHCC4323 (DSM 32826) bacteria (herein termed "ST Gal(+) bacteria");

wherein the comparative test is performed by that the ST bacteria are inoculated in skim cow milk 1% from overnight cultures and incubated for 18 hours at 37° C. and at the end of the fermentation samples are taken to measure galactose content in the fermented milk and thereby measure the reduction of excreted galactose compared to the reference CHCC4323; and (b): fermenting the milk with the bacteria of (a), wherein pH is measured during the fermentation in a way that ensures that one determines the pH values of this step (b) and wherein the fermentation is done under conditions wherein the fermentation ends with a relatively high stable pH value, defined as that the pH at the end of the fermentation is a pH from 4.3 to 4.9 and wherein the pH has not changed more than pH 0.1 during the last 2 hours of the fermentation and wherein the pH from 4.3 to 4.9 is reached before 24 hours (such as e.g. before 15 hours) of fermentation; and (c): using the fermented milk of (b) with a pH from 4.3 to 4.9 for making further adequate steps to finally end up with the produced fermented milk product.

The first aspect of the invention may alternatively be formulated as a so-called use claim—i.e. use of *Streptococcus thermophilus* (ST) Gal(+) bacteria in a method for producing a fermented milk product with a relatively high stable pH value of pH from 4.3 to 4.9 at the end of the fermentation, wherein the method is comprising following steps:

(a): inoculating at least 100 L milk with:

(I): a *Streptococcus thermophilus* (ST) bacteria composition comprising from $10^4$ to $10^{14}$ CFU/g ST bacteria cells, characterized by that the ST bacteria are able to reduce by at least 10% the amounts of excreted galactose in milk as compared to reference ST CHCC4323 (DSM 32826) bacteria (herein termed "ST Gal(+) bacteria");

wherein the comparative test is performed by that the ST bacteria are inoculated in skim cow milk 1% from overnight cultures and incubated for 18 hours at 37° C. and at the end of the fermentation samples are taken to measure galactose content in the fermented milk and thereby measure the reduction of excreted galactose compared to the reference CHCC4323; and (b): fermenting the milk with the bacteria of (a), wherein pH is measured during the fermentation in a way that ensures that one determines the pH values of this step (b) and wherein the fermentation is done under conditions wherein the fermentation ends with a relatively high stable pH value, defined as that the pH at the end of the fermentation is a pH from 4.3 to 4.9 and wherein the pH has not changed more than pH 0.1 during the last 2 hours of the fermentation and wherein the pH from 4.3 to 4.9 is reached before 24 hours of fermentation; and (c): using the fermented milk of (b) with a pH from 4.3 to 4.9 for making further adequate steps to finally end up with the produced fermented milk product.

The ST Gal(+) bacteria test according to "(a) (I)" of the first aspect may be considered a herein relevant standard test that routinely can be performed by the skilled person.

It is believed that a number of the ST Gal(+) bacteria described in above discussed prior art would comply with the ST Gal(+) test—i.e. based on the prior art and herein provided technical information it may be considered as relatively routine work to obtain ST Gal(+) bacteria that comply with the comparative test of "(a) (I)" of the first aspect.

In working Example 1 herein is described a method to obtain different ST Gal(+) bacteria complying with the comparative test of step "(a) (I)" of the first aspect—i.e. the comparative test of step "(a) (I)" of the first aspect is preferably performed according to Example 1.

As discussed above, the present inventors are not aware of a single prior art document that directly and unambiguously describes the above mentioned surprising link between ST Gal(+) bacteria and the possibility to obtain a stable relatively high pH at the end of the fermentation as such.

In line of this is step (b) a novel step as such—i.e. the prior art does not directly and unambiguously describe a method, wherein the milk is inoculated with ST Gal(+) bacteria in accordance with step (a) of the first aspect and the pH is then monitored/measured in fermentation step (b) as required in step (b) of the first aspect.

One reason for this relates to that before the present invention, the skilled person was simply not aware of the possibility that ST Gal(+) bacteria could have the herein described positive "stable relatively high pH at the end of the fermentation" effect—accordingly, the skilled person did not consider to monitor/measure the pH as required in step (b) of the first aspect in order to control/monitor this positive effect.

As understood by the skilled person in the present context—step (b) of the first aspect at least requires some kind of pH monitoring/measurements that are enough to determine that "the pH at the end of the fermentation is a pH from 4.3 to 4.9 and wherein the pH has not changed more than pH 0.1 during the last 2 hours of the fermentation and wherein the pH from 4.3 to 4.9 is reached before 24 hours of fermen-tation".

As understood by the skilled person—this pH monitoring/ measurements may be done in different ways to objectively be able to determine/evaluate the relevant pH values. For instance, it may not be required to measure pH exactly 2 hours before the end of the fermentation—for instance, if done e.g. 3 h before, 1 h before and at the end of the fermentation and the pH values at all three determinations are in the correct range then would the skilled person objectively understand that pH is also correctly within the requirement of step (b) in the last 2 hours of the fermentation. In working Examples herein (see e.g. FIG. 2 herein) were the pH monitored/measured continuously—this may be a preferred procedure.

Step (b) of the first aspect reads: "the pH at the end of the fermentation".

The skilled person knows when one is at the end of the fermentation, which essentially in the present context may be seen as relating to when the pH is not significantly dropping/lowering anymore.

As known in the art, the fermentation may end/stop when e.g. the fermentation medium does not anymore comprise enough relevant nutrients (e.g. sugars such as e.g. lactose, galactose etc.) for bacteria growth/metabolism or the fermentation may end/stop by changing the temperature (e.g. by rapid cooling) to a temperature significant different from optimal temperature for bacteria growth.

Alternatively, the fermentation ends naturally be the increasing concentration of lactic acid or other growth inhibiting compounds.

The fermenting conditions of step (b) may generally be standard suitable ST fermentation conditions in relation to a ST bacterium of interest—such as e.g. around 37° C. as used in working examples herein.

As understood by the skilled person in the present context—a reason for this relates to that it is essentially the inherent characteristic of the used ST Gal(+) bacteria as described herein that are responsible for e.g. the pH at the end of the fermentation—i.e. herein not working ST bacteria will e.g. give a final pH at the end of the fermentation of around pH 4.1 under standard ST fermentation conditions.

In view of the technical disclosure herein and the common general knowledge—it is routine work for the skilled person to select/identify at herein positive/useful ST Gal(+) strain and find suitable conditions to comply with the requirement of step (b) of the first aspect.

Step (c) of the first aspect may be seen as routine work for the skilled person—i.e. the skilled person knows how to make a fermented milk product of interest (e.g. a cheese or e.g. a yogurt).

As understood by the skilled person in the present context—in step (a) of the first aspect may the milk be inoculated with other e.g. lactic acid bacteria (LAB) of interest— for instance *L. bulgaricus* for making e.g. a yogurt (i.e. fermented milk product is e.g. a yogurt).

A second aspect of the invention relates to a method for screening and isolating a novel *Streptococcus thermophilus* (ST) bacterium cell comprising the following steps:

(i): selecting and isolating from a pool of individual ST bacteria, a new selected pool of ST bacteria that are characterized by that the ST bacteria are able to reduce galactose as required in step (a)(I) of the first aspect (herein termed "ST Gal(+) bacteria");

(ii): selecting and isolating—from the selected pool of ST Gal(+) bacteria of step (i)—a new isolated ST Gal(+) bacterium cell that is capable of giving a relatively high stable pH value at the end of the fermentation as required in step (b) of the first aspect.

Embodiment of the present invention is described below, by way of examples only.

DRAWINGS

FIG. 1: Schematic drawing of lac/gal metabolism

FIG. 2: Figure that shown that herein described ST Gal(+) bacteria had a significantly higher stable pH (around 0.3 to 0.6 points) than corresponding wildtype CHCC27806 ST Gal(–) bacteria at the end of the fermentation as such. The figure shows e.g. that the herein for the first-time deposited novel ST Gal(+) strains (CHCC28380=DSM 33158; CHCC32045=DSM 33159) have a very good stable relatively high pH at the end of the fermentation as such. For further details, see working Example herein.

FIG. 3: Figure that shown that herein described ST Gal(+) bacteria had a significantly higher stable pH (around 0.2 to 0.5 points) than corresponding wildtype CHCC4426 ST Gal(–) bacteria at the end of the fermentation as such. For further details, see working Example herein.

DETAILED DESCRIPTION OF THE INVENTION

Deposited Strains/Cells

A sample of the *Streptococcus thermophilus* cell CHCC4323 has been deposited at DSMZ (Deutsche Sammlung von Mikroorganismen und Zellkulturen GmbH, Inhoffenstr. 7B, D-38124 Braunschweig) under the accession number DSM 32826 with a deposit date of 5 Jun. 2018. The deposit has been made under the conditions of the Budapest Treaty on the International Recognition of the Deposit of Microorganisms for the Purposes of Patent Procedure.

The deposited strains below are strains that for the first time have been deposited in relation to the present application—i.e. they are novel strains as such.

A sample of the novel *Streptococcus thermophilus* cell CHCC28380 has been deposited at DSMZ (Deutsche Sammlung von Mikroorganismen und Zellkulturen GmbH, Inhoffenstr. 7B, D-38124 Braunschweig) under the accession number DSM 33158 with a deposit date of 12 Jun. 2019. The deposit has been made under the conditions of the Budapest Treaty on the International Recognition of the Deposit of Microorganisms for the Purposes of Patent Procedure.

A sample of the novel *Streptococcus thermophilus* cell CHCC32045 has been deposited at DSMZ (Deutsche Sammlung von Mikroorganismen and Zellkulturen GmbH, Inhoffenstr. 7B, D-38124 Braunschweig) under the accession number DSM 33159 with a deposit date of 12 Jun. 2019. The deposit has been made under the conditions of the Budapest Treaty on the International Recognition of the Deposit of Microorganisms for the Purposes of Patent Procedure.

As discussed in working Examples herein—the herein novel deposited strains have a very good stable relatively high pH at the end of the fermentation as such.

Accordingly, a separate aspect of the invention relates to a *Streptococcus thermophilus* cell CHCC28380 deposited with registration number DSM 33158 or a *Streptococcus thermophilus* cell CHCC32045 deposited with registration number DSM 33159.

Accordingly a further aspect of the invention relates to a *Streptococcus thermophilus* cell sharing the functional characteristics of CHCC28380 deposited with registration number DSM 33158 or a *Streptococcus thermophilus* cell sharing the functional characteristics of CHCC32045 deposited with registration number DSM 33159. In a related aspect hereto, the functional chracteristics means that the ST bacteria are able to reduce by at least 10% the amounts of excreted galactose in milk as compared to reference ST CHCC4323 (DSM 32826) bacteria (herein termed "ST Gal(+) bacteria").

A separate aspect of the invention relates to a method to obtain:

a mutant strain of *Streptococcus thermophilus* cell CHCC28380 deposited with registration number DSM 33158; or a mutant strain of *Streptococcus thermophilus* cell CHCC32045 deposited with registration number DSM 33159 comprising using the deposited strain as starting strain, making mutants of the deposited strain and isolating a novel mutant strain, wherein the mutant strain has retained the property of being ST Gal(+) of the deposited strain.

Fermented Milk Product

The milk of step (a) of the first aspect and thereby the milk of the fermented milk product the first aspect may e.g. be soy milk or animal milk (such as e.g. goat, buffalo, sheep, horse, camel or cow milk.

Preferably the milk is cow milk.

The fermented milk product is preferably a dairy product such as e.g. yogurt, cheese, kefir or buttermilk.

It may be preferred that the cheese is e.g. fresh cheese product, soft cheese product, cheddar, continental cheese, pasta filata cheese, pizza cheese or mozzarella cheese.

It may be preferred that the product is a yogurt.

Inoculating the Milk—Step (a) of First Aspect

As discussed above—in step (a) of the first aspect may the milk be inoculated also with other e.g. lactic acid bacteria (LAB) of interest—for instance *L. bulgaricus* for making e.g. a yogurt (i.e. fermented milk product is e.g. a yogurt).

It may be preferred that in step (a) of the first aspect is the milk also inoculated with from $10^4$ to $10^{14}$ CFU/g *Lactobacillus* bacteria cells (such as e.g. *Lactobacillus delbrueckii* subsp. bulgaricus)—this may be particularly relevant when the fermented milk product is e.g. a yogurt.

It may be preferred that in step (a) of the first aspect is the milk also inoculated with from $10^4$ to $10^{14}$ CFU/g *Lactococcus* bacteria cells (such as e.g. *Lactococcus lactis*)—this may be particularly relevant when the fermented milk product is e.g. a cheese.

It may be preferred that in step (a) of the first aspect is the milk also inoculated with from $10^4$ to $10^{14}$ CFU/g *Leuconostoc* bacteria cells—this may be particularly relevant when the fermented milk product is e.g. a cheese.

It may be preferred that step (a) of the first aspect relates to inoculating at least 200 L milk or inoculating at least 1000 L milk.

ST Gal(+) Bacteria of Step "(a) (I)" of First Aspect

In working Example 1 herein is described a method to obtain different ST Gal(+) bacteria complying with the comparative test of step "(a) (I)" of the first aspect.

As can be seen in Table 1 of Example 1, by use of the in this Example described special method for isolation of galactose hyper-fermenting mutants from *S. thermophilus* it was possible to obtain ST bacteria able to reduce by around 50% (see e.g. CHCC27912 and CHCC29526) the amounts of excreted galactose in milk as compared to reference ST CHCC4323 bacteria.

ST bacteria able to reduce by at least 20% the amounts of excreted galactose in milk as compared to reference ST CHCC4323 bacteria may herein be termed ST Gal(++) bacteria.

Without being limited to theory—the in Example 1 described method for isolation of galactose hyper-fermenting ST Gal(++) mutants from *S. thermophilus* may be considered special due to the fact that the galactose reduction level is dramatically increased compared to a herein termed Gal(+) strain. As described in Example 1, the galactose reduction level for CHCC14993, a Gal(+) mutant of CHCC4323, is 17%, whereas the galactose reduction level of CHCC14994, a Gal(++) mutant of CHCC4323, is 30%, compared to the wild type CHCC4323. The galactose reduction level of CHCC29526, a Gal(++) mutant from CHCC4459, is even 52% compared to the reference CHCC4323.

By using method of sub-culturing in M17-gal broth of Example 1 it was therefore possible to isolate galactose hyper-fermenting mutants with a unique galactose reducing ability.

Preferably, the ST bacteria of step "(a) (I)" of the first aspect are ST bacteria characterized by that the ST bacteria are able to reduce by at least 20% (such as at least 25%, more preferably at least 30% and even more preferably least 40%) the amounts of excreted galactose in milk as compared to reference ST CHCC4323 bacteria.

Preferably, the *Streptococcus thermophilus* (ST) bacteria cell is at least one cell selected from the group consisting of:

(a): a *Streptococcus thermophilus* cell CHCC28380 deposited with registration number DSM 33158; and (b): a *Streptococcus thermophilus* cell CHCC32045 deposited with registration number DSM 33159.

Preferably, in step "(a) (I)" of the first aspect the milk is inoculated with from $10^4$ to $10^{15}$ cfu (or from $10^4$ to $10^{14}$ cfu) (colony forming units) viable ST bacteria cells per gram milk, including at least $10^5$ cfu per gram milk, such as at least $10^6$ cfu/g milk, such as at least $10^7$ cfu/g milk, such at least $10^8$ cfu/g milk, such as at least $10^9$ cfu/g milk, such as at least $10^{19}$ cfu/g milk or such as at least $10^{11}$ cfu/g milk.

The ST bacteria cells may be a mixture of different ST strains (e.g. a mixture of herein discussed CHCC28380 and CHCC32045)—for instance $10^8$ cfu/g milk of one ST strain (e.g. CHCC28380)+$10^8$ cfu/g milk of another ST strain (e.g. CHCC32045), which in sum would imply that the milk is inoculated with $2 \times 10^8$ cfu/g milk viable ST bacteria cells.

Typically, the bacteria (e.g. a starter culture composition) are in a concentrated form including frozen, dried or freeze-dried concentrates.

As discussed in working Example herein—not all of the tested ST Gal(+) strains actually worked as required herein (i.e. gave herein discussed relatively high stable pH value at the end of the fermentation).

Accordingly and as discussed in working Example herein—a genome analysis was performed to find a common structural element among preferred positive good working ST Gal(+) strains.

The results showed that the majority of the good ST Gal(+) strains have a mutation in the −10 region/box of the promoter of the galactokinase gene (galK).

Such galK mutants are described in e.g. WO2011/026863A1 (Chr. Hansen)—as discussed above, this WO publication does not describe/relate to herein discussed "post-acidification" related problems.

Below is shown figure on page 10 of WO2011/026863A1 (Chr. Hansen):

```
CHCC11379
                                              SEQ ID NO: 5
AAAATATTGATTTTCCATGTGAAAGGGGTTATGATTTCAGTATAAACAAAAAGAATAAGTGAGATACATC

CHCC6008
                                              SEQ ID NO: 6
AAAATATTGATTTTCCATGTGAAAGGGGTTACGATTTCAGTATAAACAAAAAGAATAAGTGAGATACATC

AY7C4368
                                              SEQ ID NO: 7
AAAATATTGATTTTCCATGTGAAAGGGGTTACGATTTCAGTATAAACAAAAAGAATAAGTGAGATACATC

Consensus
                                              SEQ ID NO: 8
AAAATATTGATTTTCCATGTGAAAGGGGTTACGATTTCAGTATAAACAAAAAGAATAAGTGAGATACATC
      -35                   -10                          RBS
```

As shown in figure above and discussed in WO2011/026863A1—the wildtype/consensus sequence of the −10 region/box is "TACGAT" and strain termed "CHCC11379" comprises a mutation in −10 region/box.

The wildtype/consensus promoter sequence of the galactokinase gene (galK) is shown as SEQ ID NO:8 in figure above, which is identical to SEQ ID NO:8 herein.

In short, the skilled person can routinely determine if a ST Gal(+) strain of interest has a mutation in the −10 region/box of the promoter of the galactokinase gene (galK).

Accordingly, in a preferred embodiment the ST Gal(+) bacteria of step "(a) (I)" of first aspect are preferably bacteria that have a mutation in the −10 region of the promoter of the galactokinase gene (galK) (SEQ ID NO:8), wherein the mutation results in the replacement of one or both of C and G in the wildtype −10 region (TACGAT, SEQ ID NO:1) with a nucleotide independently selected from the group consisting of A and T.

Preferably, the mutation results in a −10 region which has the nucleotide sequence TATGAT (SEQ ID NO:2—see e.g. very positive results of e.g. CHCC28380 and CHCC32045 discussed below) or TACTAT (SEQ ID NO:4—see e.g. positive results of e.g. CHCC29248 discussed below)—most preferably, the mutation results in a −10 region which has the nucleotide sequence TATGAT (SEQ ID NO:2).

As discussed in working example herein—the herein novel deposited ST Gal(+) strains (CHCC28380=DSM 33158; CHCC32045=DSM 33159) have a very good stable relatively high pH at the end of the fermentation as such—these deposited strains comprises the mutation "TATGAT" (SEQ ID NO:2)—accordingly it is most preferred herein.

Without being limited to theory, it is believed that a higher than wildtype expression of the galK gene would give the herein discussed positive effect of getting a relatively high stable pH at the end of the fermentation—accordingly, in a preferred embodiment the ST Gal(+) bacteria of step "(a) (I)" of first aspect are preferably bacteria that have a higher than wildtype expression of the galK gene and wherein the ST Gal(+) bacteria have preferably a mutation in the −35, −10 or Ribosome Binding Site (RBS) of SEQ ID NO:8.

Fermenting the Milk with the Bacteria—Step (b) of First Aspect

Step (b) of first aspect relates to fermenting the milk with the bacteria of (a).

As discussed above, the fermenting conditions of step (b) may generally be standard suitable ST fermentation conditions in relation to a ST bacterium of interest—such as e.g. around 37° C. as used in working examples herein.

As discussed above, a reason for this relates to that it is essentially the inherent characteristic of the used ST Gal(+) bacteria as described herein that are responsible for e.g. the pH at the end of the fermentation—i.e. herein not working ST bacteria will e.g. give a final pH at the end of the fermentation of around 4.1 under standard fermentation conditions.

The skilled person knows how to ferment milk with relevant bacteria to make a fermented milk product (e.g. a cheese) of interest—accordingly, there is in the present context no need to describe this in detail.

According to the art and depending on e.g. the ST used, the fermentation temperature may e.g. be from 25° C. to 48° C., such as e.g. from 35° C. to 48° C. or such as e.g. from 36° C. to 38° C.

According to the art, the fermentation time in step (b) of the first aspect may be from 2 to 96 hours, such as from 3 to 72 hours or such as from 4 to 48 hours.

It may be preferred that the fermentation time in step (b) of the first aspect may be from 2 to 30 hours, such as from 3 to 24 hours.

Step (b) of the first aspect reads: "the pH at the end of the fermentation".

As discussed above, the skilled person knows when one is at the end of the fermentation, which essentially in the present context may be seen as relating to when the pH is not significantly dropping/lowering anymore.

As known in the art, the fermentation may end/stop when e.g. the fermentation medium does not anymore comprise enough relevant nutrients (e.g. sugars such as e.g. lactose, galactose etc.) for bacteria growth/metabolism or the fermentation may end/stop by changing the temperature (e.g. by rapid cooling) to a temperature significant different from optimal temperature for bacteria growth.

Alternatively, the fermentation ends naturally be the increasing concentration of lactic acid or other growth inhibiting compounds.

It may be preferred that the pH at the end of the fermentation is a pH from 4.3 to 4.8, such as e.g. from 4.4 to 4.8 or from 4.4 to 4.7.

In a preferred embodiment, the pH has not changed more than pH 0.05 during the last 2 hours of the fermentation.

In a preferred embodiment, the pH from 4.3 to 4.9 is reached before 15 hours (more preferably before 10 hours and even more preferably before 8 hours) of fermentation.

In relation to large scale herein relevant fermentations of milk—it is known in the art that sometimes may the fermentation of the milk be finalized within around 5 hours.

As discussed herein, the ST strain CHCC4323 (DSM 32826) may be seen as a ST reference strain that corresponds to a today commercially relevant used ST Gal(−) strains for making e.g. herein relevant dairy products.

Accordingly, in a preferred embodiment of step (b) of the first aspect the pH at the end of the fermentation is a pH that is from 0.1 to 0.8 points (preferably from 0.2 to 0.8 points, such as e.g. from 0.2 to 0.6 points) higher than a corresponding comparative pH at the end of the fermentation obtained by use of the reference ST CHCC4323 (DSM 32826) bacterium performed under comparative identical fermentation conditions.

The skilled person of course knows how to make such a comparative experiment—i.e. where fermenting in step (b) is done by use of a ST Gal(+) strain according to the first aspect and then is repeated under identical conditions with the reference ST CHCC4323 (DSM 32826) bacterium and the end pH values are then compared.

Further Adequate Steps to Make Fermented Milk Product of Interest—Step (c) of First Aspect Step (c) of first aspect relates to making further adequate steps to finally end up with the produced fermented milk product of interest.

As discussed above, the skilled person knows how to make a fermented milk product of interest (e.g. cheese or yogurt)—accordingly, there is no need to describe this in detail in the present context.

Storage of Produced Fermented Milk Product—Optional Step (d) of First Aspect As discussed above—it is believed that a higher final pH at the end of the fermentation as such would have an impact on post acidification during shelf life, which may be a significant problem with dairy products such as e.g. yogurt (see above).

Accordingly, herein discussed ST Gal(+) strains with a stable higher pH would result in lower post acidification which is a desired trait of e.g. commercial relevant dairy products.

Accordingly, in a preferred embodiment of the method of the first aspect—the method also comprises an extra step relating to:

(d): storage of the in step (c) produced fermented milk product for at least 1 day (such as at least 1 week, at least 2 weeks, at least 1 month or at least 2 months) of storage period and wherein the pH of the product at the end of said storage period is a pH from 4.3 to 4.9.

Preferably, the pH has not changed more than pH 0.3 (preferably not changed more than pH 0.2 or even preferably not changed more than pH 0.1) during the storage period.

The storage may be at the dairy producer and/or at the retailer/shop selling the fermented milk product (e.g. a yogurt).

In relation to step (d)—if the storage period of step (d) is e.g. at least one day and the pH of the product has been measured to determine that the product has a pH within the pH from 4.3 to 4.9 range of step (b) (such as e.g. pH 4.4) after one day, then has one performed step (d)—this is also true even though the product may be stored for a longer period (e.g. a year) and the product e.g. after a year has a pH below pH 4.3 (i.e. outside the range of step (d)).

The skilled person knows how to store a produced fermented milk product of interest—for instance may a yogurt be stored at e.g. from 2° C. to 10° C.—such as e.g. around 5° C.

The skilled person knows how to measure pH of a stored fermented milk product of interest and can thereby routinely determine if the conditions of step (d) are fulfilled or not.

A Method for Screening and Isolating a Novel ST Bacterium—Second Aspect

As discussed above, a second aspect of the invention relates to a method for screening and isolating a novel *Streptococcus thermophilus* (ST) bacterium cell comprising the following steps:

(i): selecting and isolating from a pool of individual ST bacteria, a new selected pool of ST bacteria that are characterized by that the ST bacteria are able to reduce galactose as required in step (a)(I) of the first aspect (herein termed "ST Gal(+) bacteria");

(ii): selecting and isolating—from the selected pool of ST Gal(+) bacteria of step (i)—a new isolated ST Gal(+) bacterium cell that is capable of giving a relatively high stable pH value at the end of the fermentation as required in step (b) of the first aspect.

Step (i) of the method of the second aspect reads "selecting and isolating from a pool of individual ST bacteria".

As known—it is routine work for the skilled person to make/create such a pool of individual bacteria cells.

It may e.g. be made from a suitable preferred starting cell, which may be subjected to suitable mutagenesis (e.g. using a chemical mutagen or UV mutagenesis) to make a pool of mutants of said starting cell—i.e. to create a pool of individual bacteria cells.

As discussed herein, in view of the technical disclosure herein and the common general knowledge—it is routine work for the skilled person to select/identify at herein positive/useful ST strain by the method for screening and isolating of the second aspect.

EXAMPLES

EXAMPLE 1: ST Gal(+) bacteria—capable of extraordinary reducing the release of galactose also in the presence of high amounts of lactose (as in milk)—i.e. ST Gal(+) bacteria of step "(a) (I)" of the first aspect

Reference Strains

ST strain CHCC4323: It has what may be termed a galK natural wildtype sequence (herein termed GalK(−)) and may be seen as a ST reference strain that corresponds to a today commercially relevant used ST strain for making e.g. cheese;

ST strain 4323-2 (CHCC14993): It comprises a mutation in the galK (galactokinase) gene (herein termed Gal(+)) and may be seen as a reference strain that corresponds to a strain made according to the description of above discussed WO2011/026863A1 (Chr. Hansen) and WO2011/092300A1 (Chr. Hansen).

Deposited Strains

CHCC14994: DSM 25838 ST strain—disclosed in WO2013/160413A1 (Chr. Hansen).
CHCC19097: DSM 32594 ST strain
CHCC19100: DSM 32595 ST strain
CHCC27912: DSM 32596 ST strain
CHCC29526: DSM 32597 ST strain
CHCC29530: DSM 32598 ST strain Some of the deposited ST Gal(+) strains are discussed in WO2019/042881A1 (Chr. Hansen)—as described above, this WO publication does not describe/relate to herein discussed "post-acidification" related problems.

Isolation of Galactose Hyper-fermenting Mutants from *S. thermophilus*

Prior to the mutant isolation the strains were streaked on M17 agar plates with 2% galactose (M17-gal plates). The wild type (wt) strains did not grow significantly on galactose as sole carbohydrate source.

Overnight cultures were then plated on M17-gal plates and several colonies could be isolated after two days of growth at 37 ° C. Several mutants were purified on M17-gal plates and retested in M17 broth containing 2% galactose as sole carbohydrate. From purified galactose positive mutants second generation galactose hyper-fermenting mutants were isolated by sub-culturing in M17-gal broth with daily 1% reinoculation from the fully outgrown overnight culture; incubation occurred at 37° C. After dilution plating, 100 single colonies were isolated from M17-gal plates and inoculated in microtitre plates with M17-gal broth. The OD was followed by an OD-reader and the clones showing a better increase of OD during 16 hours of incubation at 37 ° C. as the wt strain were further purified and characterized.

The wt *S. thermophilus* strains from which galactose-hyperfermenting mutants were isolated are:
- CHCC9861
- CHCC4459
- CHCC4426
- CHCC4323
- CHCC7018
- CHCC3050

The galactose-hyperfermenting mutants showing an unusually high galactose fermenting ability and reduced galactose excretion into the media are (mutant/wt):
- CHCC27912/CHCC9861
- CHCC29526/CHCC4459
- CHCC29530/CHCC4426
- CHCC14994/CHCC4323
- CHCC19100/CHCC7018
- CHCC19097/CHCC3050

The example includes also a typical galactose positive strain, isolated as first generation mutant from CHCC4323, named CHCC14993. CHCC14993 showed a typical galactose reduction in milk of 17% (reduction of galactose excretion in milk compared to wt CHCC4323).

Fermentation of Milk

Mutant strains were inoculated in skim cow milk 1% from overnight cultures and incubated for 24 hours at 37° C. The acidification activity of mutants was similar to the wt strain. At the end of fermentation samples were taken to measure galactose content in the fermented milk and with this the reduction of excreted galactose compared to the galactose negative reference strain CHCC4323.

Results—Analysis of Acidification and Excreted Galactose in the Fermented Milk All the tested ST strains had similar acidification profiles—i.e. the deposited ST strains of had not lost their capacity to acidify in milk.

The amounts of excreted galactose for the different tested strains are shown in Table 1 below:

Table 1 indicates the amount of galactose in fermented skim cow milk and the reduction of galactose compared to the reference CHCC4323. Whereas the typical gal+ mutant CHCC14993 showed a galactose reduction of less than 20%, the hyperfermenting mutants showed a much higher reduction of up to 52%, meaning that the amount of free galactose is much lower when e.g. pizza cheese is produced with the new mutants, which is leading to reduced browning during baking.

TABLE 1

| Average of two measurements from carbohydrate analysis. Results are shown in mg/g. | | |
| --- | --- | --- |
| Strain | Galactose | Galactose reduction (%) |
| CHCC4323 | 7.1 | 0 |
| CHCC14993 | 5.9 | 17 |
| CHCC27912 | 3.4 | 52 |
| CHCC29526 | 3.4 | 52 |
| CHCC29530 | 4.9 | 31 |
| CHCC14994 | 5.0 | 30 |
| CHCC19100 | 4.1 | 42 |
| CHCC19097 | 5.1 | 28 |

Conclusions

The results demonstrated that the deposited strains are capable of reducing the release of galactose also in the presence of high amounts of lactose (as in milk) to a degree, which is significantly improved as compared to above discussed reference strains.

EXAMPLE 2: ST Gal(+) Bacteria—pH Value at the End of the Fermentation

Strains

All the ST Gal(+) strains discussed in this Example were ST Gal(+) strains according to requirement (a) of the first aspect (i.e. claim 1) herein, wherein the comparative test is performed according to Example 1 above.

Novel Deposited Strains

The novel deposited strains below were deposited for the first time in relation to the present invention.
CHCC28380: DSM 33158 ST strain
CHCC32045: DSM 33159 ST strain

Fermentation of Milk

ST Gal(+) mutant strains and reference/wildtype ST Gal (−) strains were inoculated in skim cow milk 1% from overnight cultures in M17 with 2% lactose and incubated for 24 hours at 37° C.

The pH was monitored/measured continuously during the fermentation (intab PC logger, EasyView software).

Results

FIG. 2 herein shown that herein described ST Gal(+) bacteria CHCC28380, CHCC32045 and CHCC32046 had a significantly higher stable pH (around 0.3 to 0.6 points) than corresponding wildtype ST Gal(−) bacterium CHCC27806 at the end of the fermentation as such.

FIG. 3 herein shown that herein described ST Gal(+) bacteria CHCC29249 and CHCC29529 had a significantly higher stable pH (around 0.2 to 0.5 points) than corresponding wildtype ST Gal(–) bacterium CHCC4426 at the end of the fermentation as such. Also, at the end of fermentation the pH of CHCC4426 continuously decreases whereas the pH of the mutants CHCC29249 and CHCC29529 appeared more stable.

Herein relevant pH results of other tested strains are shown in table below.

TABLE 1

Differences in pH between ST Gal(–) wild type strains and galactose positive mutants at the end offermentation. The corresponding gal+ mutants of the wild type strains are indicated below the respective wild type strain.

| Wild type strain | Gal(+) mutant | PH after 24 hours |
|---|---|---|
| CHCC4426 | | 4.20 |
| | CHCC29248 | 4.40 |
| | CHCC29249 | 4.42 |
| | CHCC29529 | 4.44 |
| CHCC4458 | | 4.20 |
| | CHCC29231 | 4.40 |
| | CHCC29232 | 4.40 |
| | CHCC29233 | 4.40 |
| | CHCC30964 | 4.50 |
| | CHCC30962 | 4.70 |
| CHCC4459 | | 4.20 |
| | CHCC29250 | 4.40 |
| | CHCC29252 | 4.44 |
| | 4459-GAL6 | 4.20 |
| CHCC3050 | | 4.18 |
| | CHCC19098 | 4.38 |
| CHCC27806 | | 4.15 |
| | CHCC28380 | 4.48 |
| | CHCC32045 | 4.62 |
| | CHCC32046 | 4.80 |

As shown in the table above—examples of different ST Gal(+) bacteria had a significantly higher stable pH (around 0.2 to 0.6 points) than corresponding wildtype ST Gal(–) bacteria at the end of the fermentation as such.

As shown in the table above, some of the tested ST Gal(+) strains did not work as required herein (i.e. did not give herein discussed relatively high stable pH value at the end of the fermentation. As example, ST Gal(+) mutant 4459-GAL6 is included. This strain is a galactose fermenting mutant of CHCC4459. The final pH after 24 hours of incubation is, however, similar to the pH of the wild type strain after 24 hours.

The mutant with the relatively highest pH at the end of the fermentations were generally so-called galactose hyper-fermenting ST Gal(++) mutant—i.e. (as discussed above) they are able to reduce by at least 20% (such as at least 25%, more preferably at least 30% and even more preferably at least 40%) the amounts of excreted galactose in milk as compared to reference ST CHCC4323 bacteria according to Example 1 above.

Data is not shown for all tested not working ST Gal(+) strains—but around 20% of the tested ST Gal(+) strains actually worked as required herein (i.e. gave herein dis-cussed relatively high stable pH value at the end of the fermentation).

Conclusions

The results demonstrated that examples of different ST Gal(+) bacteria had a significantly higher stable pH (around 0.2 to 0.6 points) than corresponding wildtype ST Gal(–) bacteria at the end of the fermentation as such.

For a number of the tested different ST Gal(+) bacteria—the fermenting of the milk gave a relatively high stable pH value at the end of the fermentation in according with step (b) of the first aspect herein.

The data also indicated that around 20% of the tested ST Gal(+) strains actually worked as required herein (i.e. gave herein discussed relatively high stable pH value at the end of the fermentation).

The results also demonstrated that based on the technical teaching herein and the common general knowledge—it is routine screening/selection work for the skilled person to identify novel ST Gal(+) strains with the herein described positive "stable relatively high pH at the end of the fermen-tation" effect.

None of the tested ST Gal(–) strains were positive—i.e. none of these gave pH value at the end of the fermentation in accordance with step (b) of the first aspect herein.

EXAMPLE 3: Genome Analysis on Tested ST Gal(+) Strains

As discussed above—not all of the tested ST Gal(+) strains actually worked as required herein (i.e. gave herein discussed relatively high stable pH value at the end of the fermentation).

Accordingly, a genome analysis was performed to find a common structural element among preferred positive good working ST Gal(+) mutant strains.

Results

The table below show the mutations in the –10 region of the promoter of the galactokinase gene (galK) of some the strains discussed in example 2 above—i.e. both some of the positive and negative (not working) strains of Example 2 above.

TABLE 2

DNA sequences of the –10 region of the promoter of the galactokinase gene (galK) gene for galactose positive mutants compared to the wild type strains. The corresponding gal+ mutants of the wild type strains are indicated below the respective wild type strain.

| Wild type strain | Gal+ mutant | –10 galK promoter region |
|---|---|---|
| CHCC4426 | | 5'-TACGAT-3' |
| | CHCC29248 | 5'-TACTAT-3' |
| | CHCC29249 | 5'-TATGAT-3' |
| | CHCC29529 | 5'-TATGAT-3' |
| CHCC4458 | | 5'-TACGAT-3' |
| | CHCC29231 | 5'-TATGAT-3' |
| | CHCC29232 | 5'-TATGAT-3' |
| | CHCC29233 | 5'-TATGAT-3' |
| | CHCC30964 | 5'-TATGAT-3' |
| | CHCC30962 | 5'-TATGAT-3' |
| CHCC4459 | | 5'-TACGAT-3' |
| | CHCC29250 | 5'-TATGAT-3' |
| | CHCC29252 | 5'-TATGAT-3' |
| | 4459-GAL6 | 5'-TACAAT-3' |
| CHCC3050 | | 5'-TACGAT-3' |
| | CHCC19098 | 5'-TATGAT-3' |
| CHCC27806 | | 5'-TACGAT-3' |
| | CHCC28380 | 5'-TATGAT-3' |
| | CHCC32045 | 5'-TATGAT-3' |
| | CHCC32046 | 5'-TATGAT-3' |

Conclusions

The results demonstrate that herein relevant good working ST Gal(+) strains are preferably ST Gal(+) bacteria that have a mutation in the –10 region of the promoter of the galactokinase gene (galK) (SEQ ID NO:8), wherein the mutation results in the replacement of one or both of C and G in the wildtype –10 region (TACGAT, SEQ ID NO:1) with a nucleotide independently selected from the group consisting of A and T.

More preferably, the mutation results in a –10 region which has the nucleotide sequence TATGAT (SEQ ID NO:2—see e.g. very positive results of e.g. CHCC28380 and CHCC32045) or TACTAT (SEQ ID NO:4—see e.g. very positive results of e.g. CHCC29248).

The herein novel deposited ST Gal(+) strains (CHCC28380=DSM 33158; CHCC32045=DSM 33159) have a very good stable relatively high pH at the end of the fermentation as such—these deposited strains comprises the mutation "TATGAT" (SEQ ID NO:2)—accordingly it is most preferred herein.

20

REFERENCES

1. EP2957180B1 (Chr. Hansen A/S, Denmark)
2. YOFLEX® ACIDIFIX® of Chr. Hansen A/S
3. Anbukkarasi et al. (J Food Sci Technol (September 2014) 51(9):2183-2189)
4. Anbukkarasi et al. ("Production of low browning Mozzarella cheese: Screening and characterization of wild galactose fermenting *Streptococcus thermophilus* strains", International Journal of advanced research, 2013, vol. 1, no. 5, pp. 83-96)
5. Derkx et al. ("The art of strain improvement of industrial lactic acid bacteria without the use of recombinant DNA technology"; Microbial Cell Factories 2014,13 (Suppl 1))
6. WO2011/026863A1 (Chr. Hansen)
7. WO2011/092300A1 (Chr. Hansen)
8. WO2019/042881A1 (Chr. Hansen)

The invention claimed is:

1. A method for producing a fermented milk product which has reduced post acidification during storage, comprising:

(a) inoculating at least 100 L milk with a *Streptococcus thermophilus* (ST) bacteria composition comprising from $10^4$ to $10^{14}$ CFU/g ST Gal(+) bacteria, wherein the ST Gal(+) bacteria reduce the amount of excreted galactose in milk by at least 10% as compared to reference ST strain CHCC4323 (deposited at Deutsche Sammlung von Mikroorganismen und Zellkulturen GmbH (DSMZ) under accession number DSM 32826), when assessed by inoculating 1% from overnight cultures of the ST Gal(+) bacteria or reference ST strain CHCC4323 into skim cow milk and incubating for 18 hours at 37° C., and then measuring galactose content in the fermented milk at the end of the fermentation;

(b) fermenting the milk with the ST Gal(+) bacteria until the fermentation ends with a relatively high stable pH value from 4.3 to 4.9, wherein the pH does not change more than 0.1 pH units during the last 2 hours of the fermentation and wherein the pH from 4.3 to 4.9 is reached before 24 hours of fermentation, to obtain fermented milk; and (c) further processing the fermented milk obtained in (b) to obtain a fermented milk product, wherein the relatively high stable pH value from 4.3 to 4.9 in step (b) results in reduced post acidification during storage of the fermented milk product compared to a fermented milk product produced by an identical method except the milk was not fermented with ST Gal(+) bacteria.

2. The method of claim 1, wherein the milk inoculated in step (a) is cow milk and the fermented milk product is selected from yogurt, cheese, kefir and buttermilk.

3. The method of claim 2, wherein fermented milk product is yogurt.

4. The method of claim 3, wherein step (a) further comprises inoculating the milk with from $10^4$ to $10^{14}$ CFU/g *Lactobacillus* bacteria cells.

5. The method of claim 1, wherein the ST Gal(+) bacteria result in a reduced amount of excreted galactose in milk by at least 25% as compared to the reference ST strain CHCC4323 (DSM 32826).

6. The method of claim 1, wherein the ST(Gal+) bacteria comprise one or more selected from:

*Streptococcus thermophilus* strain CHCC28380 deposited with the DSMZ under accession number DSM 33158; and

*Streptococcus thermophilus* strain CHCC32045 deposited with the DSMZ under accession number DSM 33159.

7. The method of claim 1, wherein the ST Gal(+) bacteria have a mutation in a −10 region of a galactokinase gene (galK) promoter (SEQ ID NO:8), wherein the mutation results in replacement of one or both of C and G in wildtype −10 region (TACGAT, SEQ ID NO: 1) with a nucleotide independently selected from the group consisting of A and T.

8. The method of claim 7, wherein the mutation results in a −10 region which has the nucleotide sequence TATGAT (SEQ ID NO:2).

9. The method of claim 1, wherein:

step (b) further comprises measuring pH continuously until the end of the fermentation;

the fermentation temperature of step (b) is from 25° C. to 48° C.;

the fermentation time in step (b) is from 2 to 30 hours;

the pH at the end of the fermentation in step (b) is from 4.4 to 4.8;

the pH does not change more than 0.05 pH units during the last 2 hours of the fermentation of step (b) of claim 1; and the pH from 4.3 to 4.9 is reached before 10 hours of fermentation in step (b).

10. The method of claim 1, wherein the pH at the end of the fermentation in step (b) is from 0.2 to 0.8 pH units higher than the pH at the end of fermentation with the reference ST strain CHCC4323 (DSM 32826) performed under comparative identical fermentation conditions.

11. The method of claim 1, further comprising storing the fermented milk product obtained at step (c) for at least 1 week wherein the pH of the product at the end of said storage period is from 4.3 to 4.9.

12. The method claim 11, wherein storage temperature is from 2° C. to 10° C. and wherein the fermented milk product is a yogurt or a cheese.

* * * * *